(12) United States Patent
Pomerantz

(10) Patent No.: US 9,128,210 B2
(45) Date of Patent: Sep. 8, 2015

(54) METHOD TO CHARACTERIZE SHALES AT HIGH SPATIAL RESOLUTION

(71) Applicant: SCHLUMBERGER TECHNOLOGY CORPORATION, Sugar Land, TX (US)

(72) Inventor: Andrew E. Pomerantz, Lexington, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 15 days.

(21) Appl. No.: 13/969,895

(22) Filed: Aug. 19, 2013

(65) Prior Publication Data

US 2014/0048694 A1     Feb. 20, 2014

Related U.S. Application Data

(60) Provisional application No. 61/684,498, filed on Aug. 17, 2012.

(51) Int. Cl.
| | |
|---|---|
| *G01V 11/00* | (2006.01) |
| *G01N 33/24* | (2006.01) |
| *G01N 25/00* | (2006.01) |
| *G01N 21/85* | (2006.01) |

(52) U.S. Cl.
CPC ............ *G01V 11/00* (2013.01); *G01N 33/241* (2013.01); *G01N 21/85* (2013.01); *G01N 25/00* (2013.01)

(58) Field of Classification Search
CPC ........ G01V 11/00; G01N 33/24; G01N 21/00
USPC ......................................................... 250/255
See application file for complete search history.

(56) References Cited

U.S. PATENT DOCUMENTS

| | | | | |
|---|---|---|---|---|
| 4,321,465 | A * | 3/1982 | Stover et al. ................ | 250/255 |
| 2013/0182819 | A1* | 7/2013 | Dvorkin et al. .................. | 378/5 |

OTHER PUBLICATIONS

U.S. Appl. No. 13/446,975, filed Apr. 13, 2012: pp. 1-15.
U.S. Appl. No. 13/446,985, filed Apr. 13, 2012: pp. 1-15.
Bernard et al., "Multi-scale detection of organic and inorganic signatures provides insights into gas shale properties and evolution," Chemie der Erde, 2010, vol. 70(S3): pp. 119-133.
Loucks et al., "Morphology, Genesis, and Distribution of Nanometer-Scale Pores in Siliceous Mudstones of the Mississippian Barnett Shale," Journal of Sedimentary Research, 2009, vol. 79: pp. 848-861.
Slatt et al., "Pore types in the Barnett and Woodford gas shales: Contribution to understanding gas storage and migration pathways in fine-grained rocks," AAPG Bulletin, Dec. 2011, vol. 95(12): pp. 2017-2030.

* cited by examiner

*Primary Examiner* — Marcus Taningco
(74) *Attorney, Agent, or Firm* — Jakub M. Michna

(57) ABSTRACT

Apparatus and methods of characterizing a subterranean formation sample including collecting a sample from a formation, and analyzing the formation to obtain an image with 100 nm or less resolution, wherein the analyzing comprises atomic force microscopy (AFM), infrared spectroscopy (IR), and thermal analysis. Kerogen maturity, mineralogy, kerogen content, mechanical properties, and transition temperatures—including registered maps of those quantities—may be obtained in 5 minutes or less. Some embodiments may use a scanning electron microscope.

25 Claims, 5 Drawing Sheets

METHOD TO CHARACTERIZE SHALES AT HIGH SPATIAL RESOLUTION

CROSS-REFERENCE TO RELATED APPLICATION

This application claims the benefit of U.S. Provisional Patent Application Ser. No. 61/684,498 filed on Aug. 17, 2012 with the same title. The application is incorporated by reference herein.

FIELD

This application relates to characterizing subterranean formations including shale using infrared spectroscopy, atomic force microscopy, thermal analysis and microscopy.

BACKGROUND

Characterization of shales is beneficial for efficient hydrocarbon production from these resources. Shales are known to be spatially heterogeneous at small length scales (below a micron), which complicates conventional characterization techniques.

Measurements of the physical structure of shales at high resolution (around 10 nanometers) are now commonly performed using electron microscopy. For example, FIG. 1 (PRIOR ART) is an SEM image illustrating a more porous kerogen particle (top) and less porous kerogen particle (bottom), separated by about 10 microns and FIG. 2 (PRIOR ART) is an SEM image illustrating a porous kerogen particle (top) with non-porous tail (bottom right) separated by 10 microns. Measurements of mechanical properties at similar resolutions can be obtained with atomic force microscopy or nanoindentation. Measurements of chemical structure are possible at low spatial resolution (around 1 micron) using conventional infrared microscopy or Raman microscopy, potentially with near-field imaging. Other measurements of chemical composition (nuclear magnetic resonance spectroscopy) or thermal properties (transition temperature measurement) are possible in the bulk. An elegant, quick, reliable method to measure all of these properties is desirable.

FIGURES

SUMMARY

Figure 1:
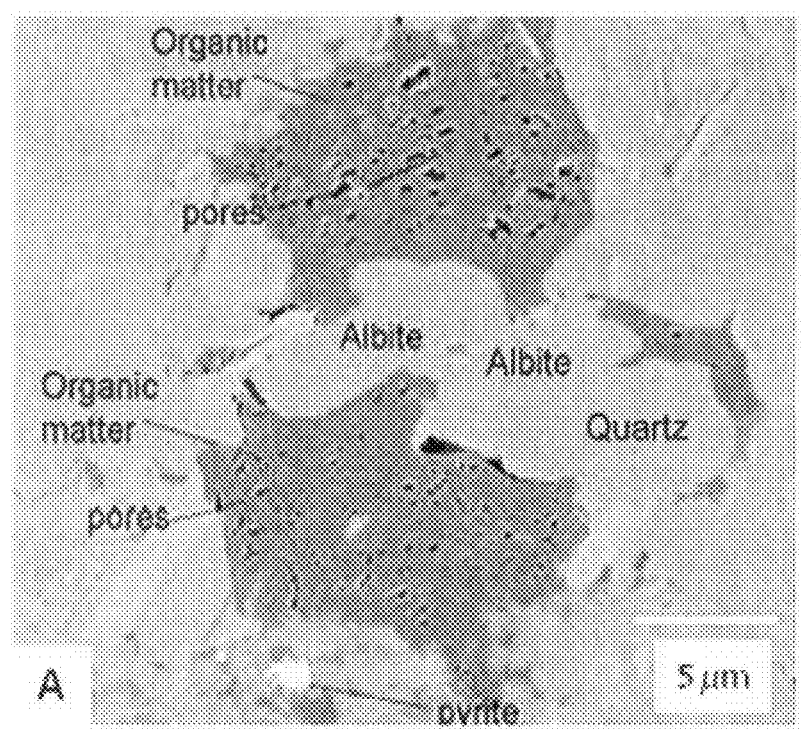
FIG. 1 (PRIOR ART) is an SEM image illustrating a more porous kerogen particle (top) and less porous kerogen particle (bottom), separated by about 10 microns.

Embodiments herein relate to an apparatus and methods of characterizing a subterranean formation sample including collecting a sample from a formation, and analyzing the formation to obtain an image with 100 nm or less resolution, wherein the analyzing comprises atomic force microscopy (AFM), infrared spectroscopy (IR), and thermal analysis. Kerogen maturity, mineralogy, kerogen content, mechanical properties, and transition temperatures—including registered maps of those quantities—may be obtained in 5 minutes or less. Some embodiments may use a scanning electron microscope.

DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range. The statements made herein merely provide information related to the present disclosure and may not constitute prior art, and may describe some embodiments illustrating the invention.

Herein we describe a method to characterize the chemical, thermal, mechanical, microstructure, and porosity properties of shale simultaneously at high resolution, that is, length scales around 100 nm or less. We describe a method to measure atomic force microscopy (AFM), infrared spectroscopy (IR), transition temperature measurement, and scanning electron microscope (SEM) at the 100 nm or less length scale for shale characterization.

AFM will provide mechanical property measurements including the following.

Compressive strength: Maximum stress a material can withstand before compressive failure (MPa)

Ductility: Ability of a material to deform under tensile load (% elongation)

Fatigue limit: Maximum stress a material can withstand under repeated loading (MPa)

Flexural modulus

Flexural strength

Fracture toughness: Energy absorbed by unit area before the fracture of material (J/m^2)

Hardness: Ability to withstand surface indentation (e.g. Brinell hardness number)

Plasticity (physics): Ability of a material to undergo irreversible deformations (-)

Poisson's ratio: Ratio of lateral strain to axial strain (no units)

Shear modulus: Ratio of shear stress to shear strain (MPa)

Shear strain: Change in the angle between two perpendicular lines in a plane

Shear strength: Maximum shear stress a material can withstand

Specific modulus: Modulus per unit volume (MPa/m^3)

Specific strength: Strength per unit density (Nm/kg)

Specific weight: Weight per unit volume (N/m^3)

Tensile strength: Maximum tensile stress a material can withstand before failure (MPa)

Yield strength: The stress at which a material starts to yield (MPa)

Young's modulus: Ratio of linear stress to linear strain (MPa)

Coefficient of friction (also depends on surface finish)

Coefficient of restitution

Roughness

Similarly, infrared spectroscopy will provide kerogen content, kerogen maturity and mineralogy. Thermal analysis will provide the transition temperature. SEM will provide microstructure and porosity. Microstructure may include physical property characteristics such as the size, shape, distribution, and connectivity of pores.

Some embodiments benefit from sample preparation including argon-ion milling to produce a flatter surface than surfaces obtained using other methods. Some embodiments may also benefit from using a fiducial, that is, a notch or landmark to align the sample to compare the results from AFM, IR, transition temperature measurement, and SEM testing. This process is known as registration. This allows registration of one pixel, one 100 nm by 100 nm region. Further, the resulting kerogen content, kerogen maturity, mineralogy, and other information may be collected and undergo registration in about 5 minutes or less.

Simultaneous measurements of AFM, IR, and transition temperature at the 100 nm lateral length scale (or below) can be performed using the photothermal induced resonance effect. This involves placing a sample in an AFM, which can be operated as a conventional AFM. Additionally, the sample can be excited with a monochromatic, tunable IR light source. When the light source is resonance with a vibration in the sample, the sample will mechanically deform as a result of the photothermal induced resonance, and that deformation can be measured at the 100 nm length scale by the AFM probe. Some embodiments may benefit from a diffuse light source. Transition temperature data can be provided by a localized heater. These measurements can be performed using an instrument such as the NANOIR™ which is commercially available from Anasys Instruments of Santa Barbara, Calif.

When applied to shales, this measurement could be used to understand the extent of spatial heterogeneity and the formation of porosity, especially in the kerogen phase. This measurement could be performed on cores or on cuttings, at the wellsite, or in the lab. A workflow for one embodiment follows.

1. Prepare samples for analysis. Samples could be core or core plugs and may be acquired with a coring tool. Samples could be cuttings which are cleaned according to U.S. patent application Ser. No. 13/446,985, filed on Apr. 13, 2012 which is incorporated herein by reference. Some embodiments may benefit from preparing the sample to have a flat surface. This could be achieved using an ion mill including argon-ion milling (Loucks, et al, Journal of Sedimentary Research 2009, Vol. 79: pp. 848-61, which is incorporated by reference herein.).

Figure 2:
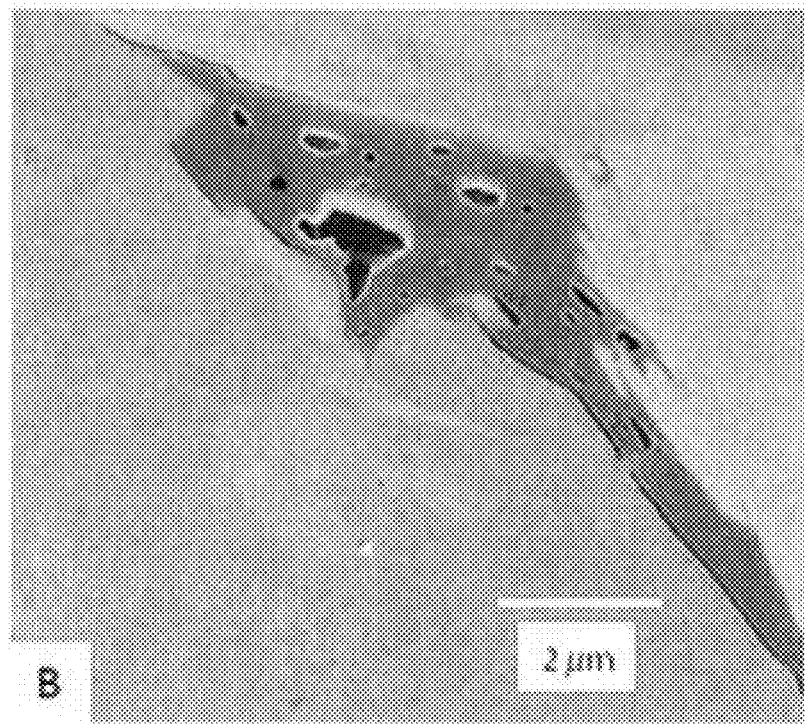
FIG. 2 (PRIOR ART) is an SEM image illustrating a porous kerogen particle (top) with non-porous tail (bottom right) separated by 10 microns.

2. Scan the sample to obtain high resolution (100 nm) AFM, IR and transition temperature maps using the photothermal induced resonance effect. Shales are heterogeneous on the 100 nm length scale, which cannot be access by traditional microspectrometry. For example, FIGS. 1 and 2 (reproduced from American Association of Petroleum Geophysicists Bulletin 95 (2011) 2017-30 and incorporated by reference herein) show pores (black), kerogen (dark gray), and minerals (light gray). The pores are seen to reside mostly in the kerogen phase. Conventional wisdom is that porosity develops with increasing maturity and that maturity varies on a length scale of miles. However, the images show higher porosity and larger pore sizes in the kerogens at the top of the image than at the bottom of the image, even though the images cover a region only about 10 microns across. The high resolution AFM and IR maps can relate that variation in pore space to variation in kerogen composition (as measured by IR), allowing for relations to be drawn between the physical structure and chemical structure. Similar relations can be made with mechanical properties (from AFM) and thermal properties (from transition temperature measurement). Some embodiments also benefit from SEM using the same sample with a fiducial.

3. As an example, maturity can be measured by examination of the lineshape of the IR peak near 2,900 cm$^{-1}$ as described in U.S. patent application Ser. No. 13/446,975, filed Apr. 13, 2012 which is incorporated by reference herein. Using that methodology, it is possible to see if there is a relationship between the porosity of the kerogen phase and the maturity of kerogen as indicated by IR on the micron length scale. Such a relation would suggest the more mature parts of the formation will be more productive.

4. As another example, it is well known that mineralogy can be measured by IR. Using that methodology, it is possible to see if there is a relationship between the porosity of the kerogen phase and the identity of the minerals adjacent to the kerogen. Such a relationship could result from mineral catalysis of kerogen maturation and would suggest that parts of the formation containing catalytic minerals (such as certain clays) will be more productive.

Figure 3:
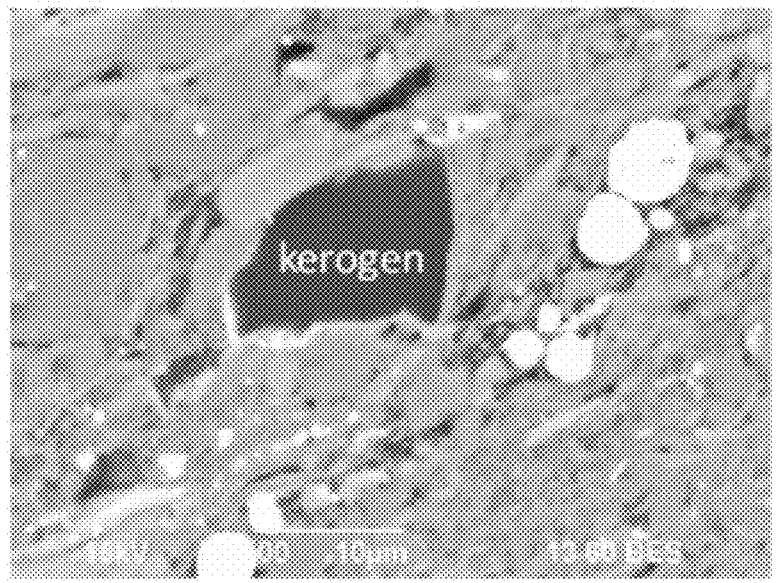
FIG. 3 is an SEM image of a sample of shale.
Figure 4:
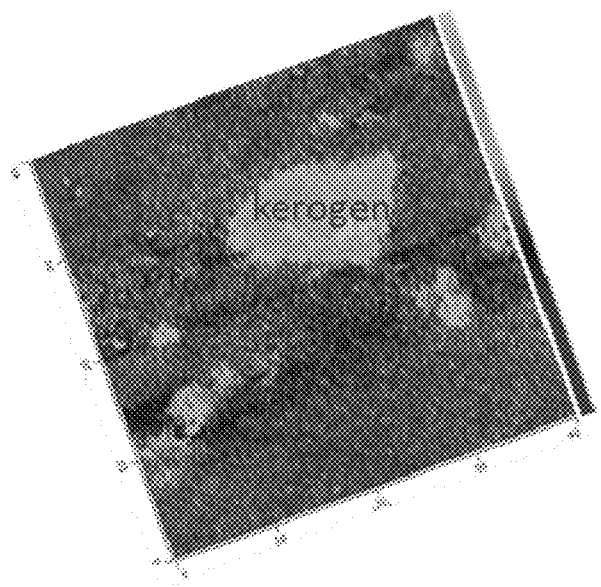
FIG. 4 is an IR image (intensity at 2,920 $cm^{-1}$) of the same sample of shale as observed in FIG. 3.

FIGS. 3 and 4 provide a SEM image (FIG. 3) and an IR image (FIG. 4) of the same sample of shale. SEM is sensitive to density and is the standard technique for finding kerogen particles in shale—the dark spot in the center is a kerogen particle. IR is sensitive to molecular absorption of infrared photons of a particular frequency, in this case near 2,920 cm$^{-1}$. The observation of this same kerogen particle demonstrates that this method can identify kerogen in shale.

Figure 5:
FIG. 5 is an IR image (intensity at 2,920 $cm^{-1}$) of an additional sample of shale.
Figure 6:
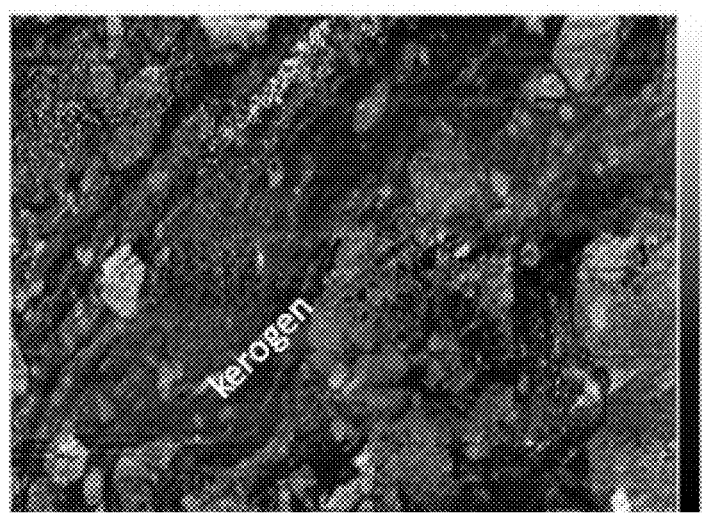
FIG. 6 is an AFM image of the same sample of shale as observed in FIG. 5.

FIGS. 5 and 6 provide an IR image (FIG. 5) and an AFM image (FIG. 6) of the same sample of shale. In the IR image, a kerogen particle is found as above, and regions composed of other materials could be found analogously. In the AFM image, the mechanical properties of different regions of the sample are measured. In this example, the measured mechanical property is hardness, but other mechanical properties could be measured analogously. The results demonstrate that this method can measure mechanical properties of shale at small length scales, and the data can be registered with compositional maps generated from the IR image.

Figure 7:
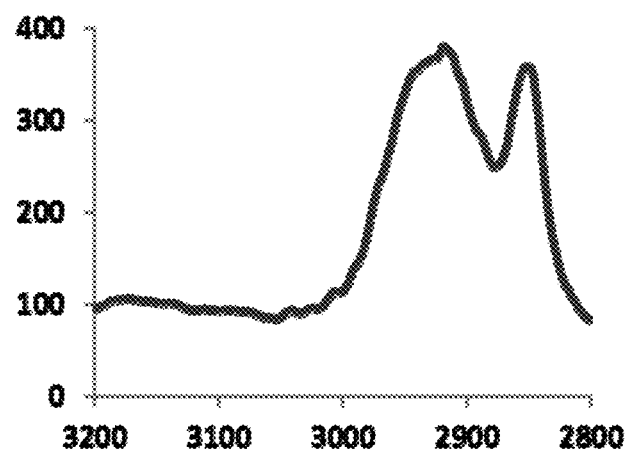
FIG. 7 is a plot of the IR spectrum obtained from an immature kerogen particle.
Figure 8:
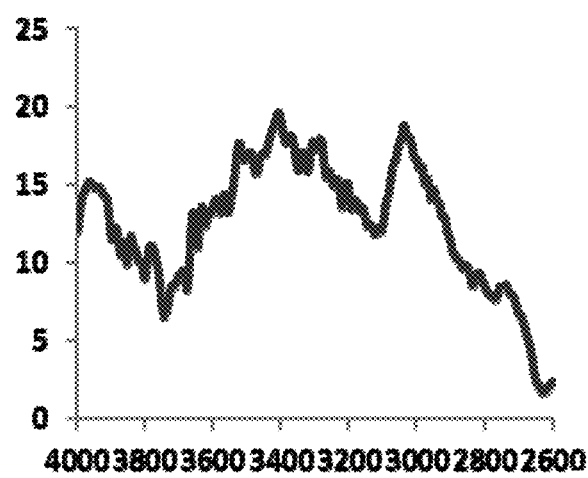
FIG. 8 is a plot of the IR spectrum obtained from a mature kerogen particle.

FIGS. 7 and 8 compare the IR spectrum obtained with our method from an immature kerogen particle (FIG. 7) and mature kerogen particle (FIG. 8). This result demonstrates that the method can measure maturity at small length scales.

As combined, this method can measure composition (identifying kerogen and minerals), mechanical properties (such as hardness), and kerogen maturity at small length scales (around 10 nm) and can allow for these measurements to be co-registered. Some embodiments may also benefit from registering thermal analysis and SEM data with these measurements.

Although several example embodiments have been described in detail above, those skilled in the art will readily appreciate that many modifications are possible in the example embodiments, without materially departing from the scope of this disclosure. Accordingly, all such modifications are intended to be included within the scope of this disclosure.

I claim:

1. A method of characterizing a subterranean formation sample, comprising:
   collecting a sample from a formation; and
   analyzing the sample to obtain an image with 100 nm or less resolution, wherein the analyzing comprises using atomic force microscopy (AFM), infrared spectroscopy (IR), and thermal analysis.

2. The method of claim 1, wherein the analyzing comprises using a photothermal induced resonance effect.

3. The method of claim 1, wherein the image comprises an image of kerogen maturity.

4. The method of claim 1, wherein the image comprises an image of mineralogy.

5. The method of claim 1, wherein the image comprises an image of kerogen content.

6. The method of claim 1, wherein the analyzing further comprises using a scanning electron microscope (SEM).

7. The method of claim 6, wherein the sample comprises a fiducial.

8. The method of claim 6, further comprising registering data obtained by the AFM, IR, thermal analysis, and SEM.

9. The method of claim 6, wherein the analyzing further comprises estimating a sample porosity from the image.

10. The method of claim 6, wherein the analyzing further comprises determining a microstructure of the sample from the image.

11. The method of claim 10, wherein the microstructure comprises at least one of a pore size, pore shape, pore distribution, and pore connectivity.

12. The method of claim 1, wherein the sample comprises a core, a core plug, or a cutting.

13. The method of claim 1, further comprising:
   preparing the sample for analysis, wherein the preparing comprises ion milling.

14. The method of claim 1, wherein the image comprises an image of a mechanical property.

15. The method of claim 14, wherein the mechanical property comprises at least one of compressive strength, ductility, fatigue limit, flexural modulus, flexural strength, fracture toughness, hardness, plasticity, Poisson's ratio, shear modulus, shear strain, shear strength, specific modulus, specific strength, specific weight, tensile strength, yield strength, Young's modulus, coefficient of friction, coefficient of restitution, and roughness.

16. The method of claim 1, wherein using infrared spectroscopy comprises using a spectrum that comprises 2,900 $cm^{-1}$.

17. The method of claim 1, wherein the analyzing occurs within 5 minutes or less of collecting the sample.

18. The method of claim 1, wherein the analyzing occurs for a 100 nm by 100 nm region of the sample.

19. A method of characterizing a subterranean formation sample, comprising:
   collecting a sample from a formation; and
   analyzing the sample to obtain an image, wherein the analyzing comprises using atomic force microscopy, using infrared spectroscopy, and generating a photothermal induced resonance within the sample.

20. The method of claim 19, wherein the analyzing further comprises using a scanning electron microscope.

21. The method of claim 19, wherein the sample comprises a fiducial.

22. The method of claim 20, further comprising registering data obtained by the scanning electron microscope with data obtained by the atomic force microscopy and the infrared spectroscopy.

23. The method of claim 19, wherein the atomic force microscopy is used to measure mechanical deformation of the sample caused by the photothermal induced resonance.

24. The method of claim 19, wherein the image comprises 100 nm or less resolution.

25. The method of claim 19, wherein the analyzing further comprises thermal analysis.

* * * * *